United States Patent [19]

Ngo

[11] Patent Number: 4,933,435

[45] Date of Patent: Jun. 12, 1990

[54] ANTIBODY PURIFICATION PROCESS

[75] Inventor: That T. Ngo, Irvine, Calif.

[73] Assignee: Bioprobe International, Tustin, Calif.

[21] Appl. No.: 333,488

[22] Filed: Apr. 5, 1989

[51] Int. Cl.[5] .................. G01N 33/53; G01N 33/543; G01N 33/544

[52] U.S. Cl. ........................................ 530/413; 435/7; 530/825; 436/501; 436/518; 436/529; 436/530; 436/532; 436/824; 436/825; 436/826

[58] Field of Search ................ 530/413; 436/824, 825, 436/826, 828, 501, 518, 529, 530, 532; 435/7

[56] References Cited

U.S. PATENT DOCUMENTS 4,704,366 11/1987 Juarez-Salinas et al. ........... 436/501

OTHER PUBLICATIONS

Scopes, R. K., *Protein Purification*, pp. 137-138 (2nd ed. 1987).

Primary Examiner—Christine M. Nucker
Assistant Examiner—Karen I. Krupen
Attorney, Agent, or Firm—Nilsson, Robbins, Dalgarn, Berliner, Carson & Wurst

[57] ABSTRACT

Immunoglobulins are purified by adsorption upon and adsorbent therefor using a buffer having a pH value of about pH 6 to pH 10 and containing at least one polycarboxylic acid in a concentration of about 0.5 M to about 0.9 M.

20 Claims, No Drawings

ANTIBODY PURIFICATION PROCESS

FIELD OF THE INVENTION

This invention relates to a process for purifying antibodies. In one of its more particular aspects, this invention relates to the purification of mammalian derived immunoglobulins.

BACKGROUND OF THE INVENTION

With the increased use of antibodies as reagents in clinical diagnostics and cancer therapy, the need has arisen for purification of such antibodies. Conventional purification techniques, in which mixtures containing antibodies are passed through a suitable column to selectively adsorb the antibodies from the mixture and the adsorbed antibodies are later eluted from the column in purified form, have been used for this purpose. However, the yield and purity of the isolated antibodies which can be obtained is limited by the lack of specificity of the column.

Previous processes for the purification of immunoglobulins, for example, suffered from the relatively low capacity of adsorbents for the immunoglobulins. In one such process, various fractions of immunoglobulins from sera of different mammalian species were adsorbed upon protein A-Sepharose ® adsorbents at pH 7 or higher and eluted at pH values ranging from pH 2.5 to pH 6.5 [R. Lindmark, K. Thoren-Tolling and J Sjoquist, "Binding of Immunoglobulins to Protein A and Immunoglobulin Levels in Mammalian Sera," *Journal of Immunological Methods*, 52:1 (1983)]. It was also known that binding of mouse IgG to protein A-Sepharose ® is pH dependent and that optimum adsorption occurs using 0.1 M sodium phosphate, pH 8.0 buffer. [P.L. Ey, S.J. Prowse and C.R. Jenkin, "Isolation of Pure $IgG_1$, $IgG_{2a}$ and $IgG_{2b}$ Immunoglobulins from Mouse Serum Using Protein A-Sepharose," *Immunochemistry*, 15:429 (1978)].

Recently, efforts have been made to increase the recovery of various immunoglobulins using specially formulated buffers. ["Mouse Monoclonal $IgG_1$, Purification with Affi-Gel$^R$ Protein A," *Bulletin* 1172, Bio-Rad Laboratories, Bio-Rad Chemical Division, Richmond, Calif. (1984)]. A process for purifying immunoglobulins using inorganic salts at concentrations within certain ranges specified for particular pH values is described in U.S. Pat. No. 4,704,366. Another process for purifying immunoglobulins using a combination of monovalent cations and polybasic anions within a specified concentration range in a buffer is described in U.S. Pat. No. 4,801,867. It would nonetheless be desirable to provide a purification process which would result in still higher yields of immunoglobulins.

Accordingly, it is an object of the present invention to provide an improved process for the purification of antibodies.

It is another object of the present invention to provide such a process which does not require additional purification steps.

A further object of the present invention is to provide a rapid, convenient and economically practical process for improving the yield of antibodies recovered in such purification by such adsorption techniques.

Other objects and advantages of this invention will become apparent from the following detailed disclosure.

SUMMARY OF THE INVENTION

The present invention provides a process for the purification of antibodies, such as immunoglobulins, which permits recovery of the purified antibodies in higher yields than have previously been realizable. The process is characterized by the use of a buffer solution containing at least one polycarboxylic acid in a concentration of about 0.5 M to about 0.9 M.

According to a preferred embodiment of the invention, there is provided a process for the purification of antibodies which includes the steps of mixing 1 part by volume of a medium containing immunoglobulins with about 0.5 to 5 parts by volume of a buffer solution having a pH value in the range of about pH 6 to about pH 10 and containing at least one polycarboxylic acid in a concentration of about 0.5 M to about 0.9 M, to provide a buffered immunoglobulin medium; and contacting the resulting buffered immunoglobulin medium with an immobilized immunoglobulin binding adsorbent to adsorb the immunoglobulins present in the buffered immunoglobulin medium. Subsequently contacting the adsorbent having immunoglobulins adsorbed thereon with a buffer solution having a pH value in the range of about pH 2 to about pH 5 serves to remove all or part of the adsorbed immunoglobulins from the adsorbent. The immunoglobulins separated from other components in the buffered immunoglobin medium may thus be recovered in substantially pure form. The yield of immunoglobulins realized according to the process of the present invention may be substantially increased, about seventy percent (70%) to more than about three hundred percent (300%), over yields previously obtainable by conventional methods.

DESCRIPTION OF THE PREFERRED EMBODIMENT

The process of the present invention is useful in purifying immunoglobulins of various types, including both monoclonal and polyclonal antibodies. It is applicable to many IgG subclasses such as $IgG_1$, $IgG_{2a}$, $IgG_{2b}$ and others. Antibodies from a wide variety of hosts including mouse, gerbil, rabbit, goat, horse, cow, and human antibodies can be purified using the process of the present invention. In general, it is applicable to any immunoglobulins for which an immunoglobulin binding adsorbent (typically, a protein) has a reasonable affinity. Immunoglobulins can be obtained from normal or immune mammalian serum, mammalian plasma, ascites fluid, hybridomas, tissue culture fluid, or any other source of antibodies.

The process of the present invention may utilize as absorbent any material which exhibits a propensity for selectively binding immunoglobulins. In particular, suitable adsorbents include immobilized protein A, immobilized protein G or similar protein adsorbents. Although it is known that various immunoglobulins (in particular, IgG from mammalian species) bind both protein A and protein G in both the purified soluble state and the formalin-fixed bacteria form, use of protein A or protein G in other than an insolubilized state is generally not as practical as the utilization of, for example, protein A or protein G immobilized upon a cross-linked agarose or other support material. Protein A or protein G in its insolubilized form can conveniently be used in a column, or in the form of a membrane, thereby facilitating the purification process.

Many suitable immunoglobulin binding immobilized protein adsorbents are commercially available. A purified protein A coupled to cross-linked agarose beads by chemically stable amide bonds can be obtained from Bio-Rad Laboratories, Richmond, Calif. as Affi-Gel®  Protein A. Protein A-Agarose is also available from Zymed Laboratories, Burlingame, Calif. This product is described as a pure protein A coupled to CNBr-activated Sepharose ® 4B. Similar products, Protein A Sepharose ® Cl-4B and Protein G Sepharose ® 4 Fast Flow are also available from Pharmacia Fine Chemicals, Uppsala, Sweden. Protein A-Ultragel ® is available from Reactifs IBF, France. It is described as a biospecific affinity chromatography sorbent able to interact with immunoglobulin G from different mammals, and is prepared by immobilizing electrophoretically pure Protein A to a glutaraldehyde-activated gel. Protein A covalently coupled to cross-linked beaded agarose is also available from Pierce Chemical Co.

A recombinant form of streptococcal protein G immobilized on agarose beads is available from Genex Corporation, Gaithersburg, Maryland as Gammabind TM G-Agarose. Immobilized recombinant protein A gel is available from Repligen Corp., Cambridge, Mass. Immobilized recombinant protein A in the form of a membrane is available, for example, as MASS ® devices from NYGene Corp., Yonkers, N.Y.

Immobilized protein A and immobilized protein G can also be provided using the techniques disclosed in U.S. Pat. No. 4,582,875, assigned to the same assignee as the present invention, the disclosure of which in its entirety is hereby incorporated by reference. This patent generally teaches the activation of hydroxyl group-containing polymeric carriers using 2-fluoro-1-methyl-pyridinium toluene-4-sulfonate (FMP). Such activated polymers are commercially available from BioProbe International, Inc., Tustin, Calif. Avid-Gel TM FMP-Activated Hydrophilic Gel T is an FMP-activated polymer of N-acryloyl-2-amino-2-hydroxymethyl-1,3-propanediol (Trisacryl GF 2000, Reactifs IBF, France). Avid-Gel TM FMP-activated Hydrophilic Gel F is an FMP-activated hydrophilic vinyl alcohol polymer composed exclusively of C, H, and O atoms (Fractogel TSK, E. Merck, Darmstadt, Germany). Both can be used to provide an immobilized protein A or immobilized protein G.

The first step in a preferred embodiment of the process of the present invention employs a buffer having a pH value in the range of about pH 6 to about pH 10, preferably a pH value of about pH 8 to about pH 9, which contains at least one polycarboxylic acid in a concentration of about 0.5 M to 0.9 M, and preferably from about 0.6 M to about 0.8 M. Any buffer otherwise suitable for use with the medium containing impure immunoglobulins can be used to provide the desired pH value. For example, phosphate buffer, glycine buffer, borate or tris buffer can be used. Phosphate buffer is especially preferred. The concentration of buffer should generally be in the range of about 0.01 M to 0.25 M.

In the context of the present invention, the term "polycarboxylic acid" is contemplated as embracing any organic acid having more than one carboxyl group, and is intended to include the salt forms thereof. The sodium and potassium salts are generally used because of availability, but other metal salts can be used as well, provided they are sufficiently soluble to provide the desired concentration of polycarboxylic acid. Ammonium salts can also be used, but are not as desirable as the alkali metal salts because of their tendency to release ammonia at higher pH values. Of course, mixtures of two or more polycarboxylic acids and/or salts thereof are equally suitable for use in accordance with this invention.

As pointed out above, the adsorbent is preferably used in a column to facilitate contact with the immunoglobulins to be purified. Prior to application of the medium containing the impure immunoglobulins to the column, the column is preferably equilibrated with several bed volumes of pH 6–10 buffer containing at least one organic polycarboxylic acid in a concentration range of about 0.6 M to about 0.9 M. This ensures that the environment is optimum for binding the immunoglobulins to the column. The medium containing the immunoglobulins to be purified, such as an immune serum or other source of immunoglobulins, is mixed with the buffer containing the at least one polycarboxylic acid in a proportion of about 1:0.5 to about 1:5 by volume, and preferably about 1:2 to about 1:4. The resulting mixture is then applied to the column, resulting in adsorption of the immunoglobulins to the column. The column is preferably then washed with additional buffer containing the at least one polycarboxylic acid in order to elute from the column impurities which are not strongly adsorbed to the column. The immunoglobulins, on the other hand, are strongly adsorbed to the column because of the enhanced affinity of the adsorbent for the immunoglobulins resulting from the presence of the buffer containing the at least one polycarboxylic acid.

Following removal of the undesired impurities according to a preferred embodiment of the invention by washing with the same buffer solution, the purified immunoglobulins may then be eluted from the column by means of a buffer having an acidic pH value, namely a pH value in the range of about pH 2.0 to about pH 5.5. The immunoglobulins can be eluted using a buffer having a pH value of about pH 3.0, which is effective to elute all of the immunoglobulins essentially simultaneously. However, if desired various fractions can be eluted by lowering the pH to a pH value between about pH 5.5 and about pH 2.0. By lowering the pH in steps, it is possible to isolate purified fractions of immunoglobulins which contain specific immunoglobulins as desired. Any buffer having an appropriate pH value can be used for elution. For example, an acetic acid-acetate buffer can be used for this purpose. A buffer concentration in the range of about 0.01 M to about 0.25 M can advantageously be used for this purpose. A buffer concentration of about 0.05 M to about 0.10 M is especially preferred.

The isolated immunoglobulins or fractions thereof can be recovered in high purity and in yields which are as much as several-fold higher than yields previously obtainable. Even yields obtained using the most sophisticated techniques previously available can be improved by using the process of the present invention.

The invention will be better understood by reference to the following examples which are intended for purposes of illustration and are not to be construed as in any way limiting the scope of the present invention which is defined in the claims appended hereto.

EXAMPLE 1

To a 3 ml column was added 1 ml of immobilized protein A (Protein A Acid Gel TM, BioProbe International, Inc., Tustin, Calif.). The column was washed at a flow rate of 1 ml per minute with 5 ml of binding buffer consisting of 0.1 M potassium phosphate buffer, pH 8, and various concentrations of potassium citrate. A quantity of 3 ml of human serum was diluted with 6 ml of binding buffer and 6 ml of the diluted sample was applied to the column at a rate of 0.5 ml per minute. Then the column was washed with 10 ml of binding buffer to rinse off serum and any unbound IgG. The immunoglobulins which were adsorbed on the column were then eluted with 5 ml of 0.1 M glycine-HCl, pH 2.8, passed through the column at a flow rate of 0.5 ml per minute. The yields of immunoglobulins, obtained by reading the O.D. of the eluate at 280 nm, ranged from about 70 percent to about 300 percent higher than that obtained using potassium phosphate alone. The results are shown in Table 1.

TABLE 1

| Binding Buffer | IgG Bound (mg/ml gel) |
| --- | --- |
| 0.1 M Potassium Phosphate | 9.22 |
| 0.1 M Potassium Phosphate + 0.6 M Potassium Citrate | 15.74 |
| 0.1 M Potassium Phosphate + 0.7 M Potassium Citrate | 23.37 |
| 0.1 M Potassium Phosphate + 0.8 M Potassium Citrate | 36.06 |
| 0.1 M Potassium Phosphate + 0.9 M Potassium Citrate | 31.04 |

EXAMPLE 2

The procedure of Example 1 was repeated using as the binding buffer 0.7 M potassium citrate in 0.1 M potassium phosphate at various pH values. The results are shown in Table 2.

TABLE 2

| pH | IgG Bound (mg/ml gel) |
| --- | --- |
| 6 | 17.14 |
| 7 | 22.98 |
| 8 | 29.38 |
| 9 | 28.30 |
| 10 | 28.16 |

EXAMPLE 3

The procedure of Example 1 was repeated using various carboxylic acids in 0.1 M sodium phosphate, pH 8.0 as binding buffer. The results are shown in Table 3.

TABLE 3

| Carboxylic Acid | | IgG Bound (mg/ml gel) |
| --- | --- | --- |
| 0.67 M | Acetate | 10.86 |
| 0.67 M | Glycine | 10.31 |
| 0.67 M | Aspartate | 13.68 |
| 0.67 M | Glutamate | 12.79 |
| 0.67 M | Malate | 14.05 |
| 0.67 M | Glutarate | 13.21 |
| 0.67 M | Succinate | 16.71 |
| 0.67 M | Tartrate | 13.38 |
| 0.67 M | Ketoglutarate | 16.92 |
| 0.67 M | N-(2-Hydroxyethyl) ethylenediamine triacetate (HEDTA) | 17.43 |
| 0.67 M | Isocitrate | 21.53 |
| 0.67 M | Citrate | 23.31 |
| 0.60 M | Ethylenediamine tetraacetate (EDTA) | 21.16 |
| 0.64 M | Ethylenediamine tetraacetate (EDTA) | 21.96 |
| 0.65 M | Ethylenediamine tetraacetate (EDTA) | 21.90 |
| 0.67 M | Ethylenediamine tetraacetate (EDTA) | 22.45 |
| 0.67 M | Ethylene glycol-0, 0'-bis (2-aminoethyl)- N,N,N',N'- tetraacetate (EGTA) | 20.47 |

In comparison to the results obtained using various polycarboxylic acids, it should be noted that the monocarboxylic acids used (acetic acid and glycine) produced results essentially comparable to the use of sodium phosphate alone (9.22 mg/ml gel).

EXAMPLE 4

The procedure of Example 1 was repeated except that an immobilized Protein G column was used.

TABLE 4

| Polycarboxylic Acid | IgG Bound (mg/ml gel) |
| --- | --- |
| 0.55 M Ethylenediamine tetraacetate (EDTA) | 24.31 |
| 0.65 M Citrate | 26.68 |

In comparison to the above results, the use of PBS alone resulted in the binding of 16 mg IgG per ml of gel.

EXAMPLE 5

The procedure of Example 1 was followed using as the binding buffer a mixture of two polycarboxylic acids in 0.1 M sodium phosphate, pH 8.0. The results are shown in Table 5.

TABLE 5

| Polycarboxylic Acid | IgG Bound (mg/ml gel) |
| --- | --- |
| 0.275 M Ethylenediamine tetraacetic acid + 0.325 M Citric Acid | 25.6 |
| None | 16.0 |

The above results clearly indicate that a combination of polycarboxylic acids was effective to enhance the binding of immunoglobulins to immobilized Protein A by about 60%, even though the concentration of each individual polycarboxylic acid was relatively low. Thus, mixtures of two or more polycarboxylic acids and/or salts thereof are clearly within the scope of the present invention, as long as the combined concentration of polycarboxylic acid is within the indicated range.

The present invention provides an important process for the purification of immunoglobulins which is rapid and convenient. Yields of immunoglobulins which are improved by 70 percent to more than about 300 percent over previous methods are realizable by practicing the process of the present invention.

The foregoing description of the invention has been directed to particular preferred embodiments for purposes of explanation and illustration. It will be apparent, however, to those skilled in the art, that many modifications and changes in the particular methods and materials may be made without departure from the scope and spirit of the invention. For example, the adsorption process can be carried out in a batchwise manner or in other buffered solutions. It is applicant's intention in the following claims to cover all such equivalents, modifications and changes that fall within the true spirit and scope of the invention.

What is claimed is:

1. In a process for the purification of immunoglobulins by contacting a medium containing said immunoglobulins with an immunoglobulin binding adsorbent, the improvement which comprises carrying out said contacting in the presence of a buffer solution having a pH value in the range of about pH 6 to about pH 10 and containing at least one polycarboxylic acid in a concentration of about 0.5 M to about 0.9 M.

2. A process according to claim 1 wherein said buffer solution which is mixed with said medium containing said immunoglobulins has a pH value of about pH 8 to about pH 9.

3. A process according to claim 1 wherein said at least one polycarboxylic acid is present in said buffer solution in a concentration of about 0.6 M to about 0.8 M.

4. A process according to claim 1 wherein said immunoglobulin binding adsorbent is an immobilized protein A or immobilized protein G.

5. A process according to claim 1 wherein said contacting is accomplished in a column of said immunoglobulin binding adsorbent.

6. A process according to claim 1 wherein said buffer solution is selected from the group consisting of phosphate buffers, glycine buffers, borate buffers and tris buffers.

7. A process according to claim 1 wherein said buffer solution has a buffer concentration in the range of about 0.01 M to about 0.25 M.

8. A process according to claim 1 wherein said buffer solution has a buffer concentration in the range of about 0.05 M to about 0.1 M.

9. A process according to claim 1 wherein said immunoglobulin binding adsorbent is protein A or protein G chemically bonded to a cross-linked agarose.

10. A process according to claim 1 wherein said immunoglobulin binding protein adsorbent is protein A or protein G chemically bonded to a 2-fluoro-1-methylpyridinium toluene-4-sulfonate activated hydroxyl group-containing polymeric carrier.

11. A process according to claim 1 wherein said medium containing said immunoglobulins is selected from the group consisting of normal mammalian serum, immune mammalian serum, mammalian plasma, mammalian ascites fluid, tissue culture fluid and material derived from a hybridoma.

12. A process for the purification of immunoglobulins which comprises:
mixing a medium containing immunoglobulins with a buffer solution having a pH value of about pH 6 to about pH 10 and containing at least one polycarboxylic acid in a concentration of about 0.5 M to about 0.9 M; and
contacting the resulting mixture with an immunoglobulin binding absorbent to absorb the immunoglobulins present in said mixture upon said adsorbent.

13. A process according to claim 12 wherein 1 part by volume of said medium containing immunoglobulins is mixed with about 0.5 to about 5 parts by volume of said buffer solution.

14. A process according to claim 12 wherein 1 part by volume of said medium containing immunoglobulins is mixed with about 2 to about 4 parts by volume of said buffer solution.

15. A process according to claim 12, further comprising washing said immunoglobulin binding adsorbent having immunoglobulins adsorbed thereon with said buffer solution.

16. A process according to claim 12, further comprising contacting said adsorbent having immunoglobulins adsorbed thereon with a buffer solution having a pH value of about pH 2 to about pH 5.5 to remove the adsorbed immunoglobulins from said adsorbent.

17. A process according to claim 16 wherein said buffer solution having a pH value of about pH 2 to about pH 5.5 is an acetic acid-acetate buffer.

18. A process according to claim 16 wherein said buffer solution having a pH value of about pH 2 to about pH 5.5 has a concentration in the range of about 0.01 M to about 0.25 M.

19. A process according to claim 12 wherein said buffer solution having a pH value of about pH 6 to about pH 10 comprises at least one compound selected from the group consisting of maleic acid, fumaric acid, succinic acid, glutaric acid, ketoglutaric acid, malic acid, tartaric acid, aspartic acid, glutamic acid, citric acid, isocitric acid, N-(2-hydroxyethyl) ethylenediamine-tetraacetic acid (EDTA), ethylene glycol-0,0-bis(2-aminoethyl)-N,N,N',N'-tetraacetic acid (EGTA) and salts thereof in a concentration of about 0.5 M to about 0.9 M.

20. A process according to claim 12 wherein the adsorbed immunoglobulins removed from the immunoglobulin binding adsorbent are recovered in substantially pure form.

* * * * *